United States Patent [19]
Shaw

[11] Patent Number: 5,897,518
[45] Date of Patent: Apr. 27, 1999

[54] FOOT AND ANKLE THERAPEUTIC COMPRESSION DEVICE

[75] Inventor: Sandra Anne Shaw, Coronado, Calif.

[73] Assignee: Circaid Medical Products, Inc., San Diego, Calif.

[21] Appl. No.: 08/559,280

[22] Filed: Nov. 15, 1995

[51] Int. Cl.⁶ ....................................................... A61F 5/00
[52] U.S. Cl. ............................... 602/65; 602/23; 602/27; 602/60
[58] Field of Search .................................... 128/881, 882; 602/20, 23, 26, 27, 60, 61, 62, 63, 64, 65, 66; 2/455, 62, 22, 908, 910, 911

[56] References Cited

U.S. PATENT DOCUMENTS

| | | | |
|---|---|---|---|
| 1,717,609 | 6/1929 | Ludwig | 602/66 |
| 3,845,769 | 11/1974 | Shaw . | |
| 4,215,687 | 8/1980 | Shaw | 602/61 |
| 4,590,932 | 5/1986 | Wilkerson | 602/65 |
| 5,120,300 | 6/1992 | Shaw . | |
| 5,254,122 | 10/1993 | Shaw . | |

*Primary Examiner*—Richard J. Apley
*Assistant Examiner*—Kim M. Lee
*Attorney, Agent, or Firm*—Harris F. Brotman

[57] ABSTRACT

A foot and ankle therapeutic compression device in which at least a pair of foot compression bands extend outwardly from opposite sides of a central region which engages the bottom of the foot and at least a pair of ankle bands extend rearwardly from the central region, and in which the pairs of foot and ankle compression bands are tightened and anchored in tightened condition by VELCRO hook and loop surfaces.

12 Claims, 3 Drawing Sheets

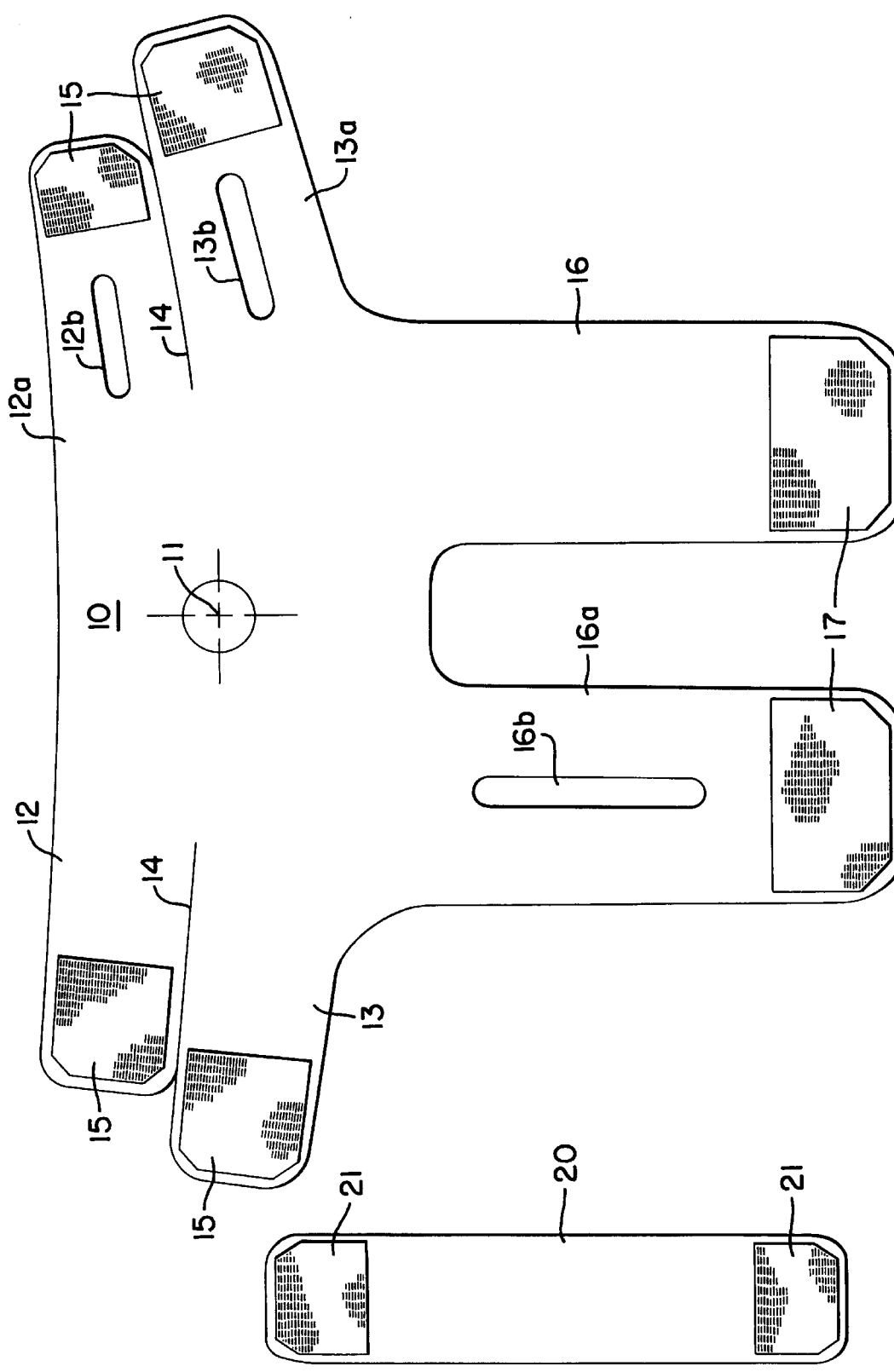

FOOT AND ANKLE THERAPEUTIC COMPRESSION DEVICE

BACKGROUND OF THE INVENTION

This invention relates to a foot and ankle therapeutic compression device capable of applying an adjustable, sustainable, essentially non-elastic compression.

Elastic and non-elastic bandaging, elastic anklets and elastic stockings are widely employed in support and compression therapy of the foot and ankle. Most suffer varying degrees of shortcomings, including ineffectiveness, difficulties in application and removal, lack of controlled adjustability, loss of compression and discomfort.

U.S. Pat. Nos. 4,215,687, 5,120,300 and 5,254,122 relate to therapeutic compression devices capable of applying therapeutic compression to the body, particularly the limbs, in which the wearer applies non-elastic therapeutic compression band by band, and the wearer can tighten the compression bands to apply firm, comfortable and controlled non-elastic pressure. This type of non-elastic compression has been clinically proven to be superior to elastic compression.

In recent years, physicians have been increasingly aware of the value of foot and ankle compression in improving blood fluid returns for reducing edema and speeding healing.

SUMMARY OF THE INVENTION

The foot and ankle therapeutic compression device of the present invention permits the wearer to easily apply a controlled level of non-elastic compression to both the foot and ankle. The comfort that this device affords and the ease with which the wearer can maintain a controlled non-elastic compression level at all times is an important advantage over conventional foot and ankle devices.

The foot and ankle therapeutic compression device of the present invention is made of essentially non-elastic fabric having a VELCRO outer loop surface and an inner surface which, for the most part, is smooth. The device includes a central region for engaging the arch of the sole of the foot, one or more pairs of wrap around foot compression bands extending outwardly in opposite directions from both sides of the central region, one of the bands having a slot so that an opposite band can be threaded through the slot to apply controlled compression to the foot and both bands having VELCRO hook surfaces at the ends of the inner surface so that they can be anchored to the outer loop surface to maintain the controlled compression. The device also includes a pair of spaced-apart ankle compression bands extending rearwardly from the device, one of said ankle compression bands having a slot to permit the other ankle band to be threaded through it and pulled apart to apply a controlled compression to the ankle, the bands also having VELCRO hook surfaces at the ends on the inner surface to permit them to be anchored to the outer loop surface to maintain the compression applied to the ankle.

As an additional feature, a cross ankle compression band having VELCRO hook surfaces on the inner surface of each end can be applied across the top of the ankle to establish cross ankle compression.

DESCRIPTION OF DRAWINGS

FIG. 1 is a plan view of the inner surface of the foot and ankle therapeutic compression device of the present invention;

FIG. 2 is a view of the inner surface of the cross ankle compression band;

DESCRIPTION OF PREFERRED EMBODIMENTS

Figure 3:
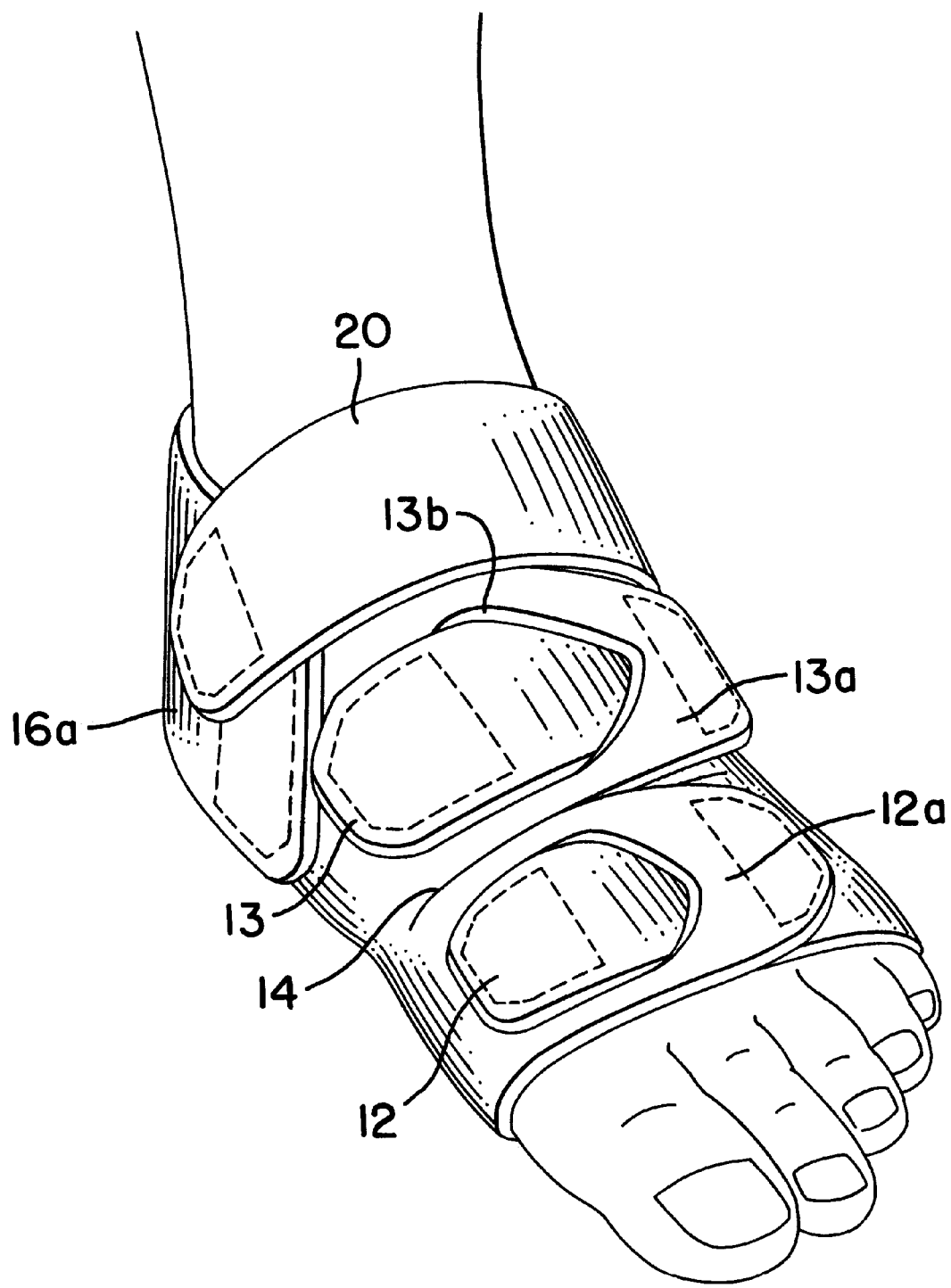
FIG. 3 is a perspective view showing the device and cross ankle compression band as applied to the foot and ankle.

The foot and ankle therapeutic compression device, as shown in FIG. 1, is made of a non-elastic or limited stretch fabric having a VELCRO loop outer surface and an inner foot engaging smooth surface, for example, VELCRO VELTEX, VELCRO Laminate or Velcro #3610 fabric which has a nylon loop outer surface, an intermediate core such as polyester foam and a backing such as nylon tricot. If a limited stretch fabric is used, for example, a fabric of 10% to 15%. stretch or less, the fabric will invariably be stretched to its limit in its application, so that the fabric is essentially inelastic when it has been tightened during application.

The device includes a central region 10 for engaging the bottom of the foot, preferably marked with suitable indicia 11, such as crossed lines, to help center the device under the arch of the foot. Pairs of wrap around compression bands extend outwardly in opposite directions from both sides of the central region and cooperate to apply compressions to different, adjacent portions of the foot. More specifically, one pair of compression bands 12, 12a applies compression to a forward portion of the foot and a pair of bands 13, 13a applies compression to a portion of the foot immediately adjacent a rearward portion of the foot when they are tightened. The bands 12 and 13, on one hand, and 12a and 13a, on the other hand, are separated by slits 14, so that when the bands are tightened, the compression will be applied uniformly to the entire portion of the foot which the bands encompass. The bands 12a and 13a contain slots 12b and 13b to permit the respective bands 12 and 13 to be threaded through the respective slots above the foot before the ends of the bands are pulled apart to apply the desired compression. VELCRO hook surfaces 15 are carried at the ends of each of the bands 12, 12a, 13 and 13a on the inner surfaces thereof to permit them to be anchored in tightened condition to the outer loop surface.

A pair of spaced-apart ankle compression bands 16, 16a extends rearwardly from the central region 10. These bands are shown in parallel relation, but they may extend at angles to each other. These bands both carry VELCRO hook surfaces 17 at the ends on the inner surface. The band 16a contains a slot 16b to permit the band 16 to be threaded therethrough before the band ends are pulled apart to apply compression to the back of the ankle and the hook surfaces are brought forward to anchor them against the outer loops surface.

In the application of the device to the foot, as shown in FIG. 3, the center of the underside of the foot arch is placed over the center cross lines 11 on the inner surface. The bands 12 and 12a are brought around the top of the foot, and the band 12 is threaded through the slot 12b of the band 12a. The ends of the bands are then pulled in opposite directions to apply the desired compression, and their hook surfaces 15 are pressed against the outer loop surfaces of the bands 12 and 12a to anchor them and maintain the controlled compression.

This procedure is repeated for the bands 13, 13a. The band 13 is threaded through the slot 13b of the band 13a above the foot, the ends of the bands are pulled apart to apply the controlled compression and the hook surfaces 15 are pressed against the outer loop surfaces of the bands to anchor them in place to maintain the controlled compression.

In the application of the ankle bands 16, 16a, the bands 16, 16a are lifted upwardly with the application of the bands 13, 13a, the band 16 is threaded through the slot 16b in the band 16a, the bands are brought around the back of the ankle, pulled to establish the desired compression and their hook surfaces 17 are pressed against the loop surfaces of the foot bands to anchor them and maintain the controlled compression.

If it is desired to apply additional compression across the upper arch of the ankle, this can be accomplished by a cross arch compression band 20 shown in FIG. 2. The band is made of non-elastic material, for example, of the same fabric as the foot and ankle compression device described above, with VELCRO hook surfaces 21 on the inner surface at each end. The hook surface 21 at one end of the cross-arch band is anchored to the outer loop surface of one of the bands 16, 16a, and it is then pulled across the upper arch of the ankle to apply the desired compression before the hook surface 21 at the other end of the band is anchored to the outer loop surface of the other ankle compression band.

Figure 4:
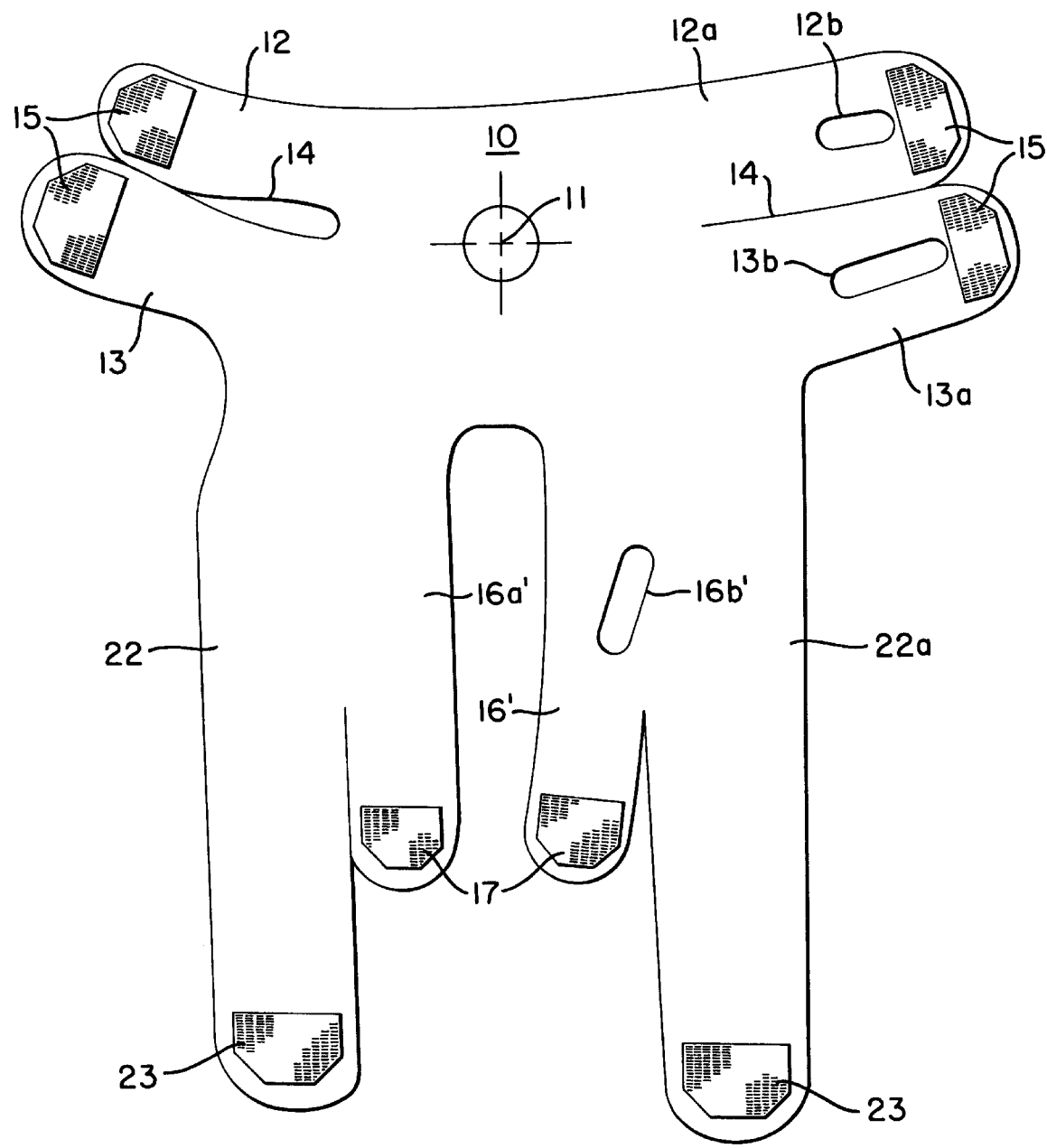
FIG. 4 is a plan view of the inner surface of another embodiment of the foot and ankle therapeutic compression device of the present invention.

In the alternative embodiment shown in FIG. 4, two additional ankle bands 22, 22a are provided, both extending rearwardly from the compression device 10 outside bands 16, 16a. At least a portion of the band 22 extends rearwardly from the rear edge of the band 13, and at least a portion of the band 22a extends rearwardly from the rear edge of the band 13a, so that the bands 22, 22a at their forward ends are lifted upwardly when the bands 13, 13a are lifted to thread and tighten them. The bands 22, 22a have VELCRO hook surfaces 23 at their ends on the inner surface.

The compression device of FIG. 4 is applied in the same manner as the device described in connection with FIGS. 1 to 3. After the ankle bands 16', 16a' are applied, the bands 22 and 22a are wrapped tightly one at a time, around the Achilles heel and above the ankle bone, and they are anchored by pressing the hook surfaces 23 against the outer loop surface of the foot bands to hold them tightly in place. The bands 22, 22a apply compression to a region of the ankle above the region to which the bands 16' and 16a' apply compression.

One of the bands 22, 22a can be provided with a slot (not shown) to permit them to be threaded together before being tightened in the manner of the other pairs of bands.

The therapeutic compression device of the present invention is preferably made of a relatively flexible material so that male band can easily pass through the slot of the female band when tightening them. It is, therefore, not necessary to diminish the widths of portions of the male bands, as in the above-identified prior art patents, to facilitate threading and tightening the male and female bands.

The therapeutic compression device of the present invention provides a simple, easy to apply means for maintaining an effective controlled non-elastic compression to a portion of the body that does not readily accommodate conventional non-elastic compression devices, and it is effective in applying non-elastic compression to the very difficult to heal foot and ankle ulcer and in supporting a sprained ankle.

The invention has been shown and described in preferred forms and by way of example, and it is apparent that many variations and modifications can be made therein. The invention is not intended to be limited to any specified form or embodiment except insofar as such limitations are expressly set forth in the claims.

I claim:

1. A foot and ankle therapeutic compression device made of essentially non-elastic fabric having a VELCRO loop outer surface and an inner surface, the device comprising a central region for the inner surface to engage the sole of the foot, at least one pair of foot compression bands extending outwardly in opposite directions from both sides of the central region to encompass the foot, a slot in one of the foot bands of the pair to accommodate an opposite band in threaded relationship, a pair of spaced-apart ankle compression bands extending rearwardly from the device and VELCRO hook surfaces at the ends of the inner surface of each of the foot and ankle compression bands, whereby opposite outwardly extending foot bands can be lifted above the foot, one band can be threaded through the slot of the other, both foot bands can be tightened and their inner hook surfaces can be anchored to the outer loop surfaces to maintain a controlled compression, and the rearwardly extending ankle bands can be tightened against the back of the ankle and the inner hook surfaces anchored to the outer loop surface to maintain them in tightened condition.

2. A therapeutic device as set forth in claim 1 including a slot in one of the ankle compression bands to accommodate the other ankle compression band in threaded relationship.

3. A therapeutic compression device as set forth in claim 1 in which the fabric is flexible and has a smooth inner surface.

4. A therapeutic compression device as set forth in claim 3 which includes a padding between the inner and outer surfaces.

5. A therapeutic compression device as set forth in claim 1 in which there are at least two pairs of foot compression bands for applying compression to adjacent portions of the foot.

6. A therapeutic compression device as set forth in claim 5 in which the foot compression bands on each side of the central region are separated by a slit so that each set of foot compression bands can be tightened separately to apply the desired compression to different, adjacent parts of the foot.

7. A therapeutic compression band as set forth in claim 1 including an essentially non-elastic cross-arch band having hook surfaces on the inner surface at each end of the band to anchor the cross-arch band to the outer loop surfaces of the ankle compression bands.

8. A therapeutic compression device as set forth in claim 1 in which at least portions of the pair of ankle compression bands extend rearwardly from the central region.

9. A therapeutic compression device as set forth in claim 1 in which at least portions of the pair of ankle compression bands extend rearwardly from portions of the device which are lifted upwardly against the ankle with the foot compression bands when they are lifted.

10. A therapeutic compression device as set forth in claim 1 which includes an outer pair of spaced-apart ankle compression bands extending rearwardly from the device and an inner pair of spaced-apart ankle compression bands extending rearwardly from the device and interposed between the outer pair of bands.

11. A therapeutic compression device as set forth in claim 10 in which each of the outer bands extends rearwardly from a portion of the device which is lifted upwardly with a foot compression band and at least portions of the inner bands extend rearwardly from portions of the central region which are lifted with the application of a pair of foot bands.

12. A therapeutic compression device as set forth in claim 10 including a slot in at least one of the inner ankle compression bands for threading the other inner band of the pair through it for tightening the pair of inner bands around the back of the ankle.

* * * * *